(12) United States Patent  (10) Patent No.: US 8,262,989 B2
Carlsson et al.  (45) Date of Patent: Sep. 11, 2012

(54) MICRO-CALORIMETER APPARATUS

(75) Inventors: Thomas Carlsson, Uppsala (SE); Kjell Rosengren, Hässelby (SE)

(73) Assignee: Senzime AB (Publ.), Uppsala (SE)

( * ) Notice: Subject to any disclaimer, the term of this patent is extended or adjusted under 35 U.S.C. 154(b) by 1401 days.

(21) Appl. No.: 10/333,410

(22) PCT Filed: Jul. 23, 2001

(86) PCT No.: PCT/SE01/01664
§ 371 (c)(1),
(2), (4) Date: Aug. 20, 2003

(87) PCT Pub. No.: WO02/08710
PCT Pub. Date: Jan. 31, 2002

(65) Prior Publication Data
US 2004/0028112 A1  Feb. 12, 2004

Related U.S. Application Data

(60) Provisional application No. 60/219,932, filed on Jul. 21, 2000.

(51) Int. Cl.
*G01N 25/20* (2006.01)
(52) U.S. Cl. .......................................................... 422/51
(58) Field of Classification Search ...................... 422/51
See application file for complete search history.

(56) References Cited

U.S. PATENT DOCUMENTS

| 4,021,307 A | | 5/1977 | Mosbach | |
|---|---|---|---|---|
| 4,255,961 A | * | 3/1981 | Biltonen et al. | 374/11 |
| 4,492,480 A | | 1/1985 | Wadsö et al. | |
| 5,114,862 A | * | 5/1992 | Brenneman | 436/169 |
| 5,163,753 A | * | 11/1992 | Whiting et al. | 374/10 |
| 5,487,870 A | * | 1/1996 | McKinney et al. | 422/73 |
| 5,494,826 A | * | 2/1996 | Stetter et al. | 436/147 |
| 5,547,282 A | * | 8/1996 | Pinhack et al. | 374/36 |
| 5,707,149 A | * | 1/1998 | Freire et al. | 374/33 |
| 5,958,349 A | | 9/1999 | Petersen et al. | |
| 6,017,494 A | * | 1/2000 | Ashihara et al. | 422/58 |

FOREIGN PATENT DOCUMENTS

| WO | WO93/01489 | 1/1993 |
|---|---|---|
| WO | 98/38487 | 9/1998 |
| WO | 98/50147 | 11/1998 |

* cited by examiner

*Primary Examiner* — In Suk Bullock
*Assistant Examiner* — Paul Hyun
(74) *Attorney, Agent, or Firm* — Young & Thompson

(57) ABSTRACT

A micro-calorimeter apparatus comprises a thermostated housing (3,4,5); a pair of essentially flat heat sinks (9,10), suspended in the housing (2) and thermally floating relative to the environment inside the housing (3,4,5). The heat sinks (9,10) are arranged with their surfaces facing each other. A pair of Peltier elements (11) are thermally attached to the heat sinks (9,10), one element (11) on each heat sink (9,10), on the facing surfaces, forming a gap between them for the accommodation of a generally flat biosensor unit (12).

16 Claims, 8 Drawing Sheets

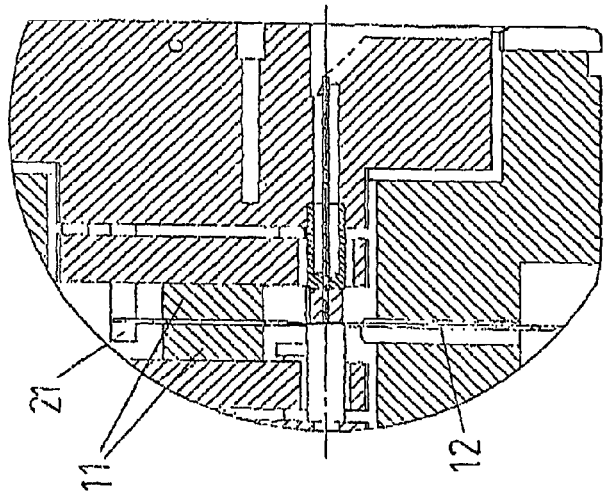
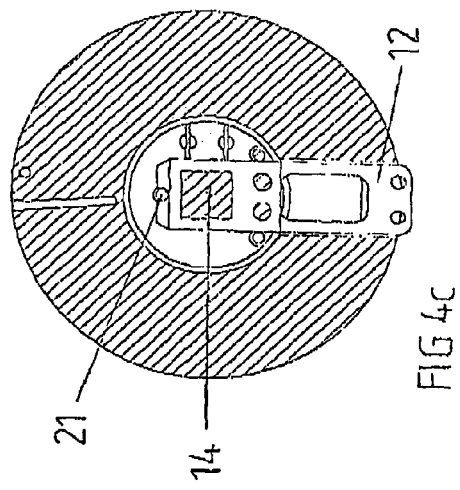
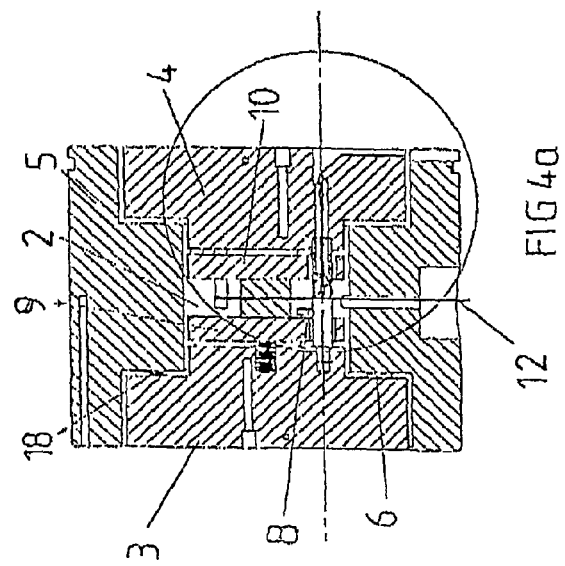

MICRO-CALORIMETER APPARATUS

This application is a national stage application of PCT/SE01/01664 filed Jul. 23, 2001, which claims benefit of Application No. 60/219,932 filed on Jul. 21, 2000.

BACKGROUND OF THE INVENTION

1. Field of the Invention

The present invention relates to biosensor systems in general, and in particular to a calorimetric type of system, especially for enzymatic reactions.

2. Description of the Related Art

The term biosensor is commonly referred to as a measuring device that combines a biological sensing part in close proximity to a non-biological transducer which converts the biochemical or electrochemical information produced in the biological part into a measurable signal.

The most commonly employed transducer in current biosensor instruments (e.g. a clinical analyser) today is electrochemically based. An clinical analyser is often used in connection with a biosensor unit (one-time use), which before operation, is connected to the analyser. The biosensor unit contains both the biological and the electronic transducer. It has turned out that there is a significant cost of designing and fabricating a custom integrated biosensor unit that includes both the biological sensing part and the necessary electronic elements. One major reason for this is that the materials and methods used for electronic components require very high temperatures, which temperature levels are incompatible with the fabrication of the biological part. It has turned out to be difficult to combine these contradicting demands of the devices to be manufactured.

SUMMARY OF THE INVENTION

In order to eliminate the drawbacks associated with the prior art devices it is suggested according to the present invention to separate the biological parts from the electronic parts in the biosensor unit. This can be achieved by using a new thermal transducer technology.

When the analysis is to be carried out the biosensor unit itself is easily connected and brought in thermal contact with the transducer in the instrument.

Thereby, only the requirements and limitations set by the biological system need to be considered in the manufacturing process of the biosensor unit. Also, packaging of the biosensor unit should thereby be simplified.

The invention defines a micro-calorimeter apparatus comprising a thermostated housing; a pair of essentially flat heat sinks, suspended in said housing and thermally floating relative to the environment inside the housing, and arranged with their surfaces facing each other; and a pair of Peltier elements thermally attached to said heat sinks, one element on each heat sink, on said facing surfaces, forming a gap between them for the accommodation of a generally flat biosensor unit. The term "generally flat" indicates that at least the reaction chamber of such a biosensor unit should be flat in the meaning that the thickness of such a chamber and the opposite large walls enclosing it is substantially smaller than to the dimensions of said large walls. The calorimeter as well as the biosensor unit shall be designed so as to enable a continuous flow of a sample of bio fluid through the reaction chamber. Therefore, the calorimeter as well as the biosensor unit comprises suitable channels for this purpose. Heat produced by the reaction between fluid and enzymes is transmitted via the opposite large walls of the chamber to the respective Peltier element, thereby making it possible to measure the reaction.

Preferably, the Peltier elements are arranged so as to be in a heat conducting contact with thin foils defining opposite walls of a reaction chamber defined by the biosensor unit when the biosensor unit is in an operative position between the Peltier elements. Inside the reaction chamber, enzymes adapted for the reaction are arranged. A basic principle of the invention is that the heat transmitting area between Peltier elements and reaction chamber walls should be as large as possible in relation to the volume of the reaction chamber. Therefore, the thickness of the reaction chamber is small in relation to the dimensions of the walls defined by the foils.

For best performance of the calorimeter the heat conducting contact area between Peltier elements and the foils should correspond to the total reaction chamber wall area defined by said foils. Total chamber wall area is referred to as the total area of the outer surface of the chamber wall-forming part of the foils directed towards the respective Peltier element.

According to a preferred embodiment at least one of the Peltier elements is movable to and from the other Peltier element in order to facilitate insertion of the biosensor unit between the Peltier elements.

Preferably the housing comprises a plurality of metal blocks, at least one of which acts as a thermostat element, for the purpose of providing a generally constant air temperature around the heat sinks and the Peltier elements during operation of the calorimeter.

The heat sinks are suspended in said housing by means of heat insulating members connected to a respective block.

At least one of the heat sinks should be moveable in relation to the block connected thereto along the insulating member on which it is suspended.

Preferably, the calorimeter comprises a force element, such as a spring, exerting a force, preferably a spring force, on the movable heat sink towards the other heat sink for the purpose of pressing an inserted biosensor unit against the other heat sink and belonging Peltier element. The force element spring also enables withdrawal of the movable heat sink/Peltier element for the purpose of facilitating insertion or removal of the bio sensor unit.

According to one embodiment, the housing is defined by two opposite blocks and a cylinder located between said opposing blocks, each heat sink being connected to a respective one of the opposing blocks. The cylinder is hollow in order to accommodate the heat sink/peltier element units as well as the biosensor unit. In this particular embodiment the insulating members comprise holding pins made of a material presenting a low heat conductivity.

Preferably, the inventive calorimeter also comprises members for snap fitting the biosensor unit in its operative position, thereby facilitating fitting of the biosensor unit in the calorimeter.

The invention also relates to a biosensor unit, characterized in that it comprises a generally flat reaction chamber the external surfaces of which are adapted to fit snugly between the Peltier elements of a calorimeter apparatus as defined above.

Further features and advantages of the invention are presented in the following detailed description of preferred embodiments and in the annexed patent claims.

BRIEF DESCRIPTION OF THE DRAWINGS

FIG. 3b illustrates the holder portion with the reaction chamber covered with a thin foil, seen from opposite direction in relation to FIG. 3a;

FIG. 4a is an axial cross sectional view of the biosensor apparatus;

FIG. 4b is a close-up view of a biosensor unit according to the present invention in thermal contact with Peltier elements;

FIG. 4c is a cross sectional view of the biosensor unit positioned to a pin 21;

DETAILED DESCRIPTION OF THE INVENTION

The principle of calorimetry, i.e. the detection of heat of reaction, on which the present invention is based is well known since many years.

Figure 1:
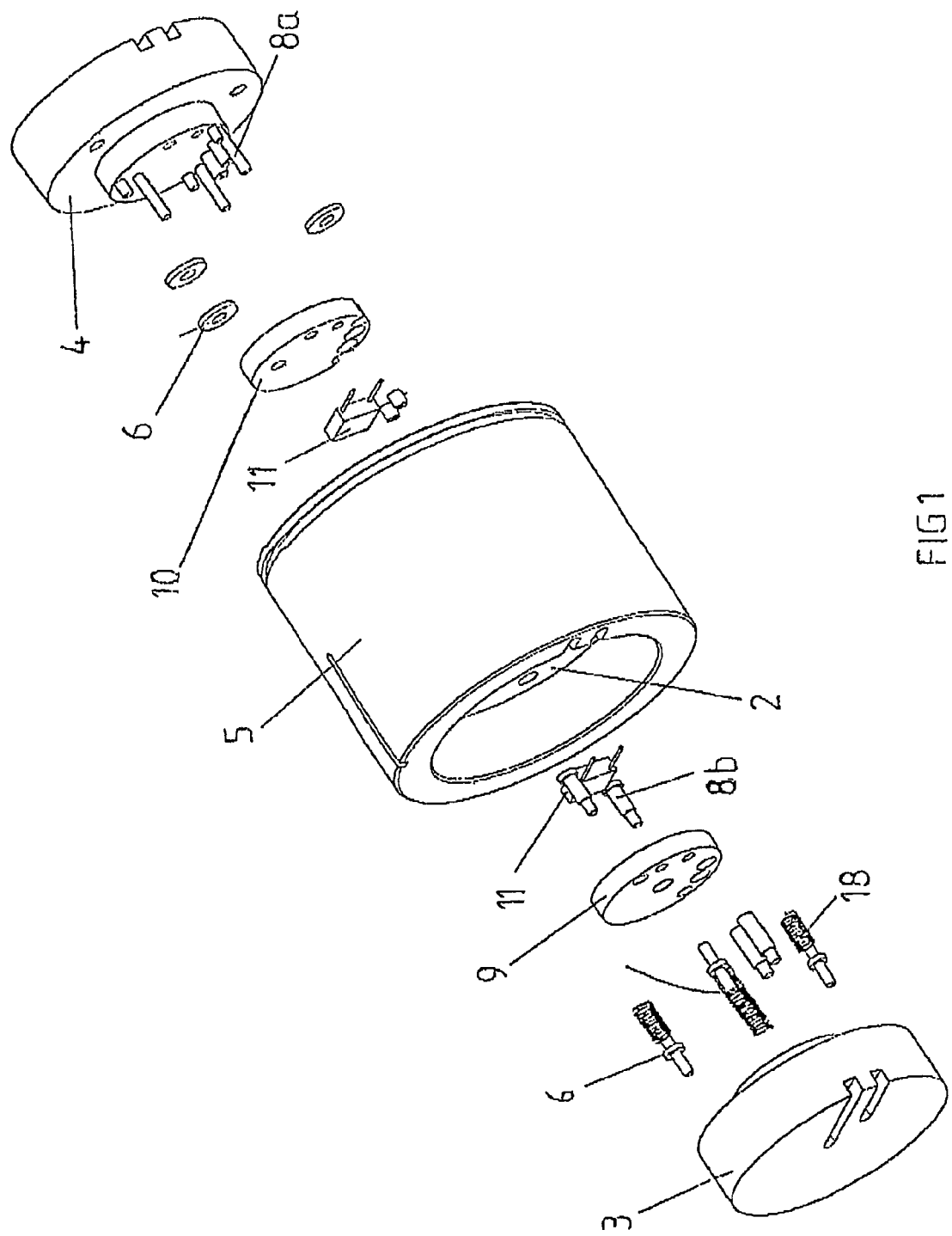
FIG. 1 is an exploded view, showing a biosensor apparatus according to the present invention.
Figure 2:
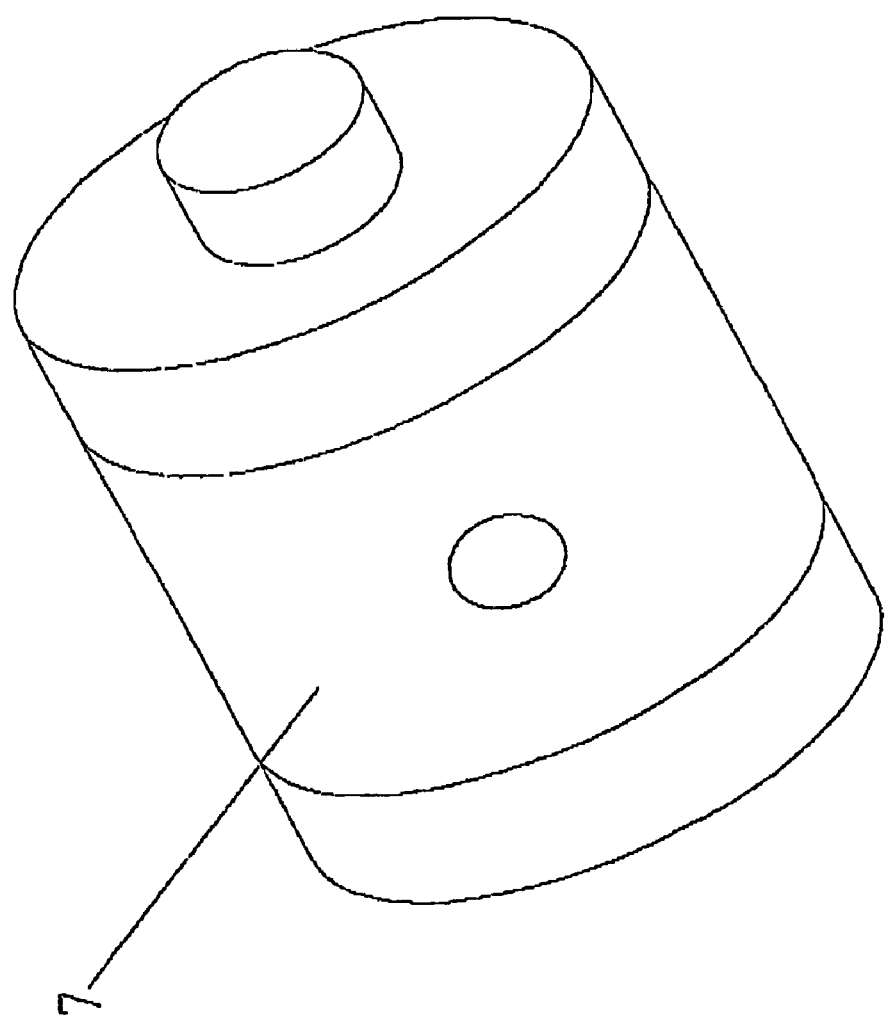
FIG. 2 illustrates the biosensor apparatus with an insulating house attached.

The apparatus according to the invention is schematically illustrated in FIG. 1 and is generally described with 1. The apparatus comprises a thermostated space or compartment 2, formed from, or defined by, two opposing blocks 3,4 and a cylinder 5, where the block 3 is axially moveable a short distance in relation to the cylinder 5 and the block 4 is fixed to the cylinder 5. The two blocks and the cylinder is separated from each other by separating members, here small washers 6, thereby forming an insulating air gap between them. Each part is individually temperature controlled. The entire device is enclosed in an insulating house 7, see FIG. 2. The two blocks are provided with holding pins 8a,8b made of a material with low heat conductivity, preferably plastics onto which are placed two heat sinks 9,10, heat sink 9 being slightly moveable in relation to its block 3 along the two holding pins 8b, whereas the heat sink 10 is fixed to its block.

The heat sink are circular plates made of a material having a large heat capacity, such as aluminium. The heat sinks are located so as to form a space between them. They are also provided in such a way that they "thermally float" with respect to the compartment, by the provision of an air gap surrounding the heat sinks. The expression "thermally floating" should be taken to mean that the heat exchange between the heat sink and the thermostated compartment are kept minimal. This is achieved by suspending the heat sinks inside the compartment onto the holding pins. On each heat sink there is mounted a Peltier element 11 in very good thermal contact with the heat sink. The Peltier elements are attached to the heat sinks such that they face each other. The unit of heat sink/Peltier element attached to one 3 of the blocks 3,4 is to some extent also movable.

Figure 3A:
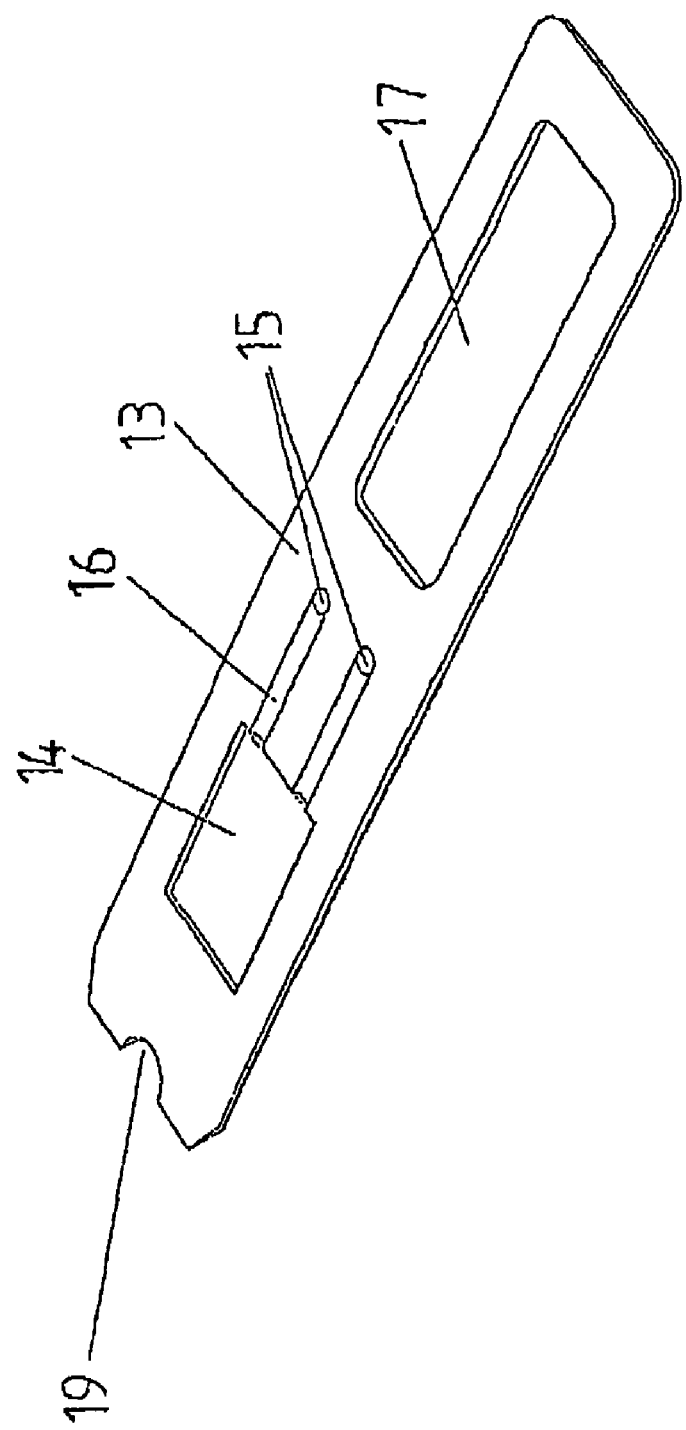
FIG. 3a shows a holder portion of the biosensor apparatus with a reaction chamber open.

The biosensor unit 12 shown in FIG. 3a to be used with the apparatus comprises a holder portion 13 and a reaction chamber 14, provided as an integral part of the holder portion 13. The reaction chamber 14 is an essentially flat structure with two opposing surfaces between which the reaction chamber is formed. Inlet and outlet of fluid flow is achieved through two openings 15 in the holder and the fluid channels 16, etched in the holder. In order to minimize thermal transportation through the holder it has an open structure 17, in it.

Here is shown one example of a biosensor unit design. The overall detailed design of the biosensor unit with holder, reaction chamber and fluid channels is a matter of which type of specific reaction it is applied for. The example shown here is approximately 50×10×0.5 mm, but the right dimensions and overall design should be optimized for each special case.

Figure 3B:
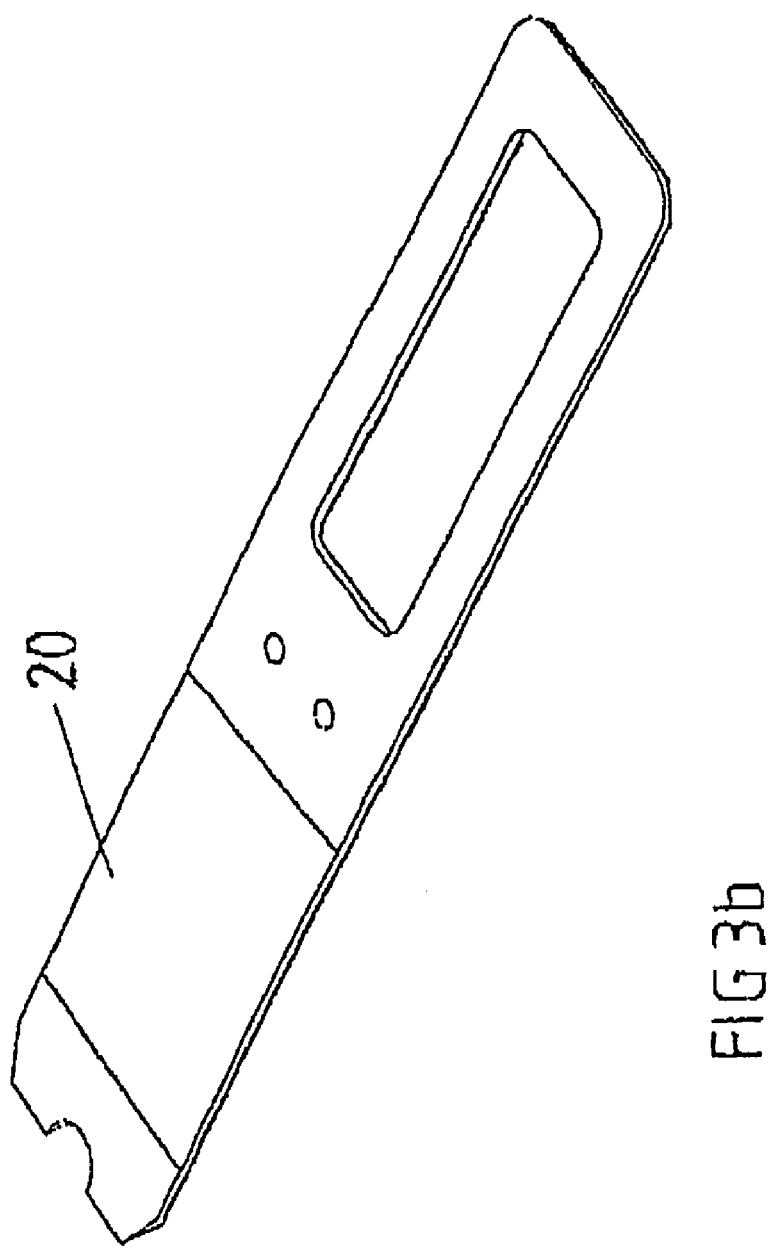

The reaction chamber 14 is covered on each side by a thin foil 20 (see FIG. 3b) made of a polymeric material, e.g. a polyimide. This polymer is very strong and can thus be made very thin, yielding a very high rate of heat conduction through it, which is essential for the invention. Between the foils 20 there can be provided support materials on which e.g. an enzyme can be immobilized, by methods known in the art. The distance between the surfaces should be as small as possible, and the lower limit is only set by manufacturing/technological limitations. A practical upper limit for the thickness of the active matrix in the reaction chamber is probably about 1 mm.

The biosensor unit is preferably made of a polymeric material. Any material that can be easily processed to the desired structure is suitable.

The thickness of the reaction chamber 14 (from one external surface to another) corresponds closely to the distance between the opposing Peltier elements, for reasons to be discussed below.

The apparatus according to the invention is operated as follows.

By virtue of the heat sink/Peltier element aggregate being attached to the moveable block 3, it can easily be moved by the decompression of springs 18, such that the gap between the aggregates is slightly widened (see FIG. 4a). Thereby it will be an easy matter to insert the biosensor unit 12 between them. When the holder has been inserted to an extent that grooves 19 of the holder and a pin 21 meet, the biosensor unit will be "snap-fitted" in position. Grooves 19 and pin 21 thereby define snap fitting members. When the biosensor unit is in its block 3, it is moved together with its heat sink/Peltier element by compression of the three springs 18. When the block is in its inner position its heat sink/Peltier element press, by action of the springs 18, the biosensor unit to the fixed heat sink/Peltier element. Then the two Peltier elements will rest against the external surfaces of the reaction chamber in very good thermal contact. The reaction chamber of the biosensor unit and the Peltier elements will only be separated by the thin foils 20 mentioned above, thereby ensuring excellent heat transfer from the reaction chamber to the Peltier elements.

Figure 5:
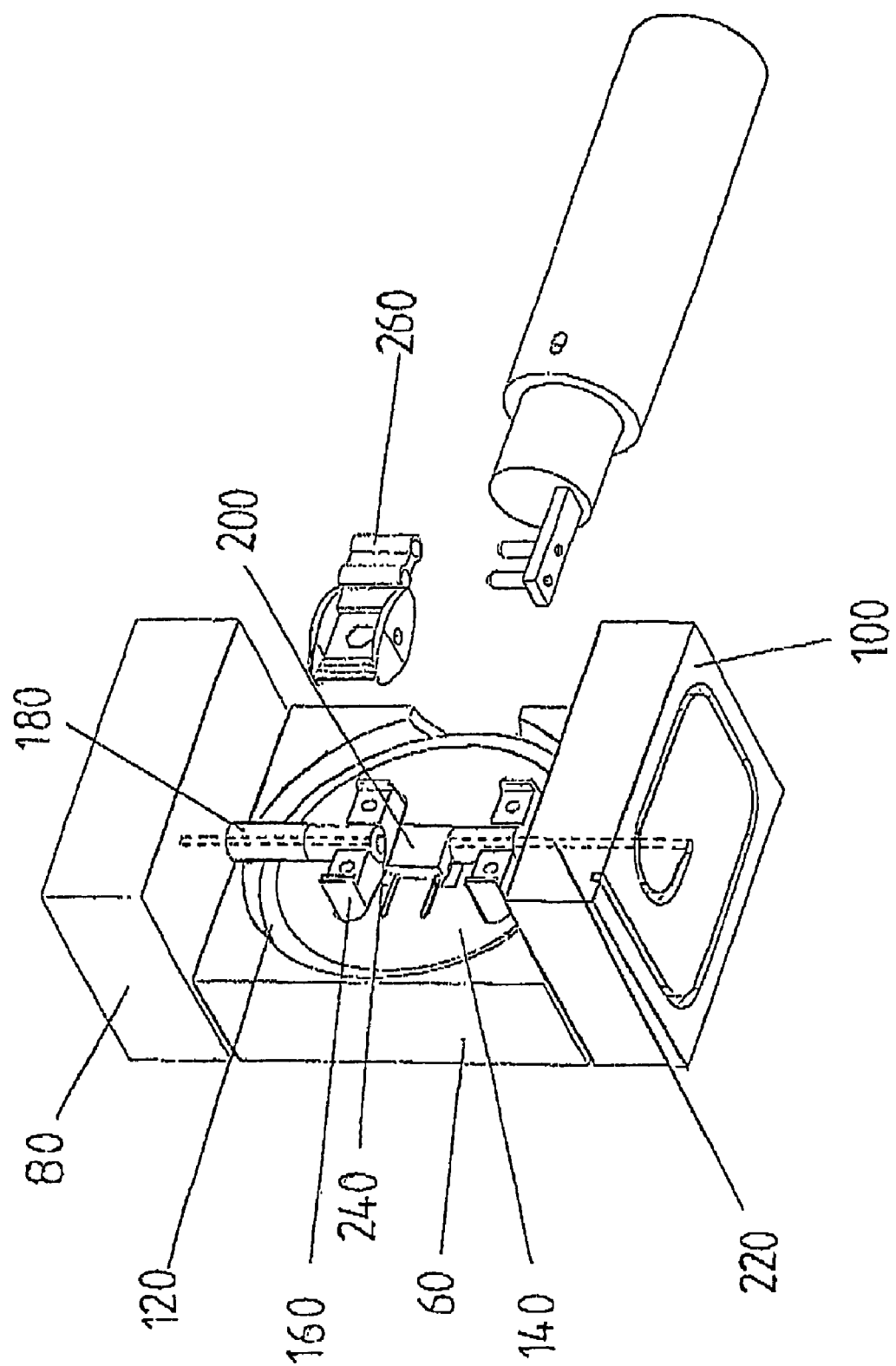
FIG. 5 is a perspective view, partly broken away, showing an alternative embodiment of the biosensor apparatus according to the invention.

The alternative biosensor apparatus 30 according to the invention is schematically shown in FIG. 5 (the upper portion omitted for clarity). It comprises a thermostated space or compartment 40 formed from a number of metal blocks 60, 80, 100, at least one of which, preferably two, act as thermostat elements 80, 100. The entire device is enclosed in an insulating housing (not shown). Two opposing blocks 60 (only one shown) have depressions 120 formed in the surfaces thereof in which there are provided two moveable heat sinks 140 (only one shown). The heat sinks are circular plates made of a material having a large heat capacity, such as aluminium.

The heat sinks are located so as to form a space between them. They are also provided in such a way that they "thermally float" with respect to the compartment, by the provision of an air gap surrounding the heat sinks. This is achieved by suspending the heat sinks inside the compartment in insulating yokes 160. The yokes are journalled on shafts 180 extending from the thermostat blocks 80, 100. On each heat sink there is mounted a Peltier element 200 in very good thermal contact with the heat sink. The Peltier elements are attached to the heat sinks 140 such that they face each other. Each unit of heat sink/Peltier element is to some extent movable by the yokes 160 being pivotally mounted as indicated above.

The journalling shafts 180 have a further function, namely to provide flow channels 220 (indicated with broken lines) for a flowing medium to be analyzed in the instrument. The flow channels extend through the thermostat blocks and terminates in a spherically shaped end surface 240 located at the end of said shafts.

Figure 6A:
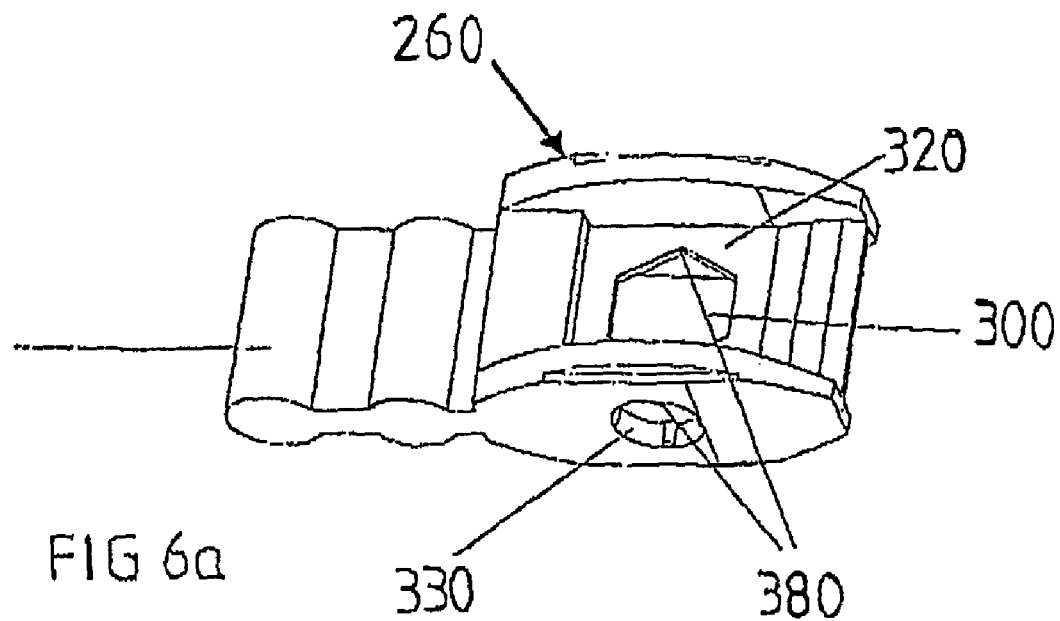
FIG. 6a is a perspective view of the alternative biosensor unit.
Figure 6B:
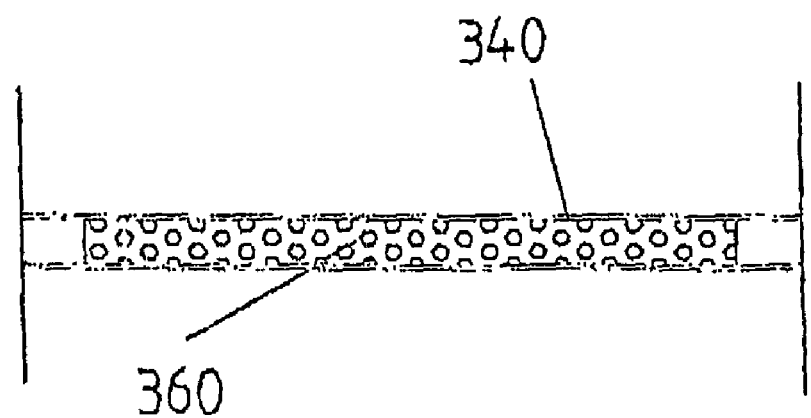
FIG. 6b is a schematic cross-section through an alternative embodiment of the reaction chamber according to the present invention.

The alternative biosensor unit 260 according to the invention is shown in FIG. 6*a* to be used with the alternative biosensor apparatus 30 and comprises a holder portion 280 and a reaction chamber 300 provided as an integral part of the holder. The reaction chamber is an essentially flat structure with two opposing surfaces between which the reaction compartment is formed. The holder has a generally "H"-shaped cross-section where the web 320 joining the legs of the "H" has an opening made in it. The web portion is covered on each side by a thin foil 340 (shown in FIG. 6*b*) of a polymeric, preferably non-electrically conducting material, e.g. polyimide. This polymer is strong and can thus be made thin (not more than half, preferably not more than $1/10$ of the thickness of the reaction chamber (here 0.3-0.5 mm)), thereby having a high rate of heat conduction through it, which is essential for the invention. Between the foils there can be provided a support material, for example beads 360, on which e.g. an enzyme, anti bodies or anti genes can be immobilized, by methods known in the art. This general principle is also preferably applied to the first embodiment described above. The distance between the surfaces should be as small as possible, and the lower limit is only set by manufacturing/technological limitations. A practical upper limit for the thickness of the active matrix in the reaction chamber is probably about 1 mm. The sensor structure is preferably made of a polymeric material. Any material that can be easily processed to the desired structure is suitable.

The holder forms two opposing flat side surfaces 320 oriented essentially perpendicularly with respect to the flat reaction chamber part. In these side surfaces there are through holes 380 provided, exiting inside the reaction chamber 300 for the introduction of a flowing sample. The channel openings on the side surfaces of the holder are slightly recessed 330 to match the spherically shaped end part 240 of the shaft. The thickness of the reactor (from one external surface to another) corresponds closely to the distance between the opposing Peltier elements, for reasons to be discussed below.

The apparatus according to the invention is operated as follows.

Figure 7:
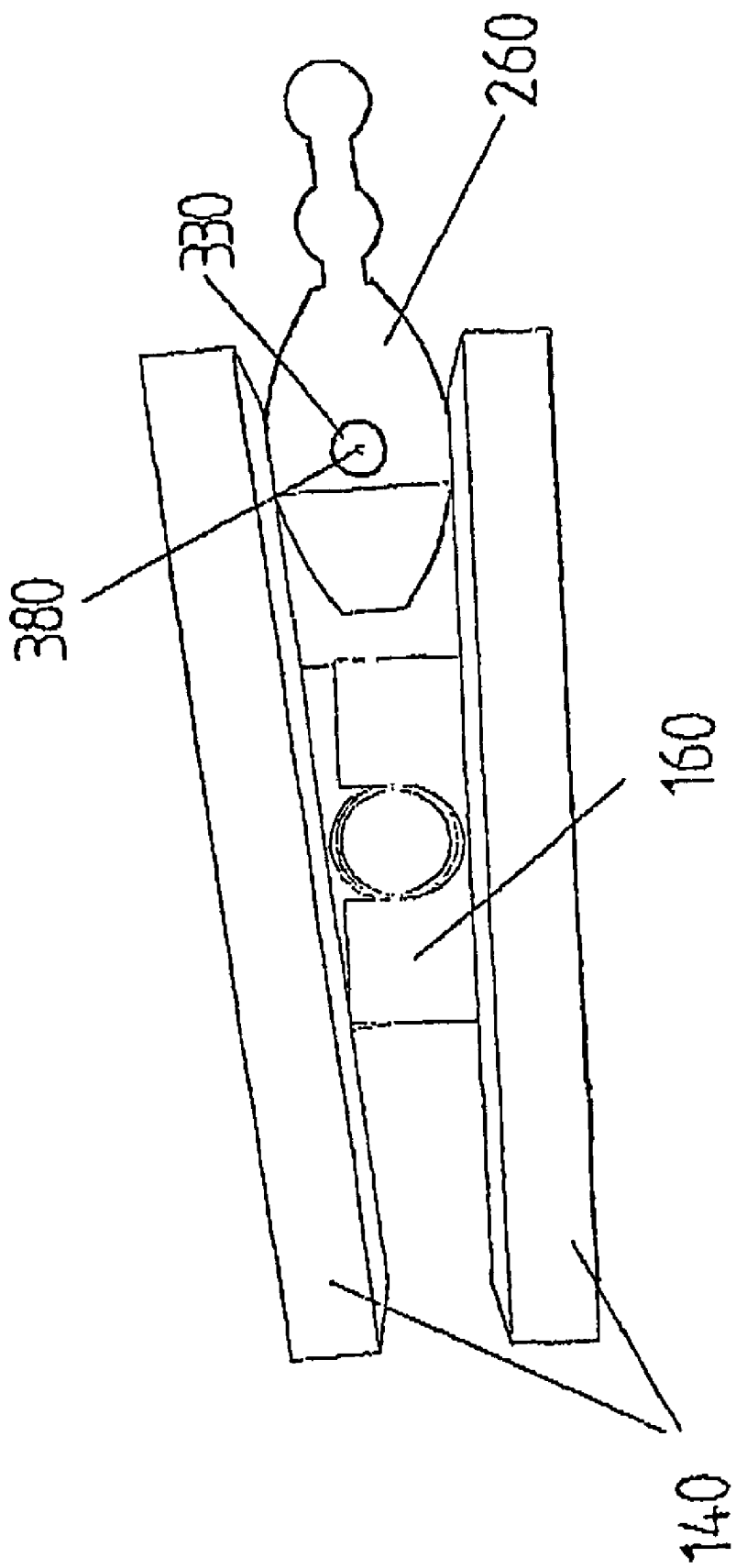
FIG. 7 is a schematic illustration of the positioning of the alternative biosensor unit.

By virtue of the heat sink/Peltier element aggregates being pivotally hinged, they can easily be moved such that the gap between them is slightly widened (see FIG. 7). Thereby it will be an easy matter to insert the biosensor structure 260 between them. When the holder has been inserted to an extent that the recesses 330 of the channel openings and the protrusions 240 meet, the sensor will be "snap fitted" in position, and then the Peltier elements 200 will rest against the external surfaces of the reactor chamber in very good thermal contact.

The heat developed in the reaction chamber by e.g. an enzyme reaction will give rise to a heat flow from the reaction chamber (hot side) to the heat sinks (cold side). This heat flow will be taken up and dissipated very quickly by the heat sinks, and eventually released from them very slowly. This is made possible by selecting the heat capacity of the heat sinks such that the thermal impact from the heat flow on the heat sinks is minimized. In the present arrangement the thermal disturbance is of the order of <1-100 ppm. Due to the large heat capacity of the heat sinks the heat evolved in the reaction chamber will in practice not affect the temperature in the reaction chamber. Because the heat sinks are "thermally insulated" from their immediate environment they will provide for a uniform heat flow being created from the reaction chamber to the heat sinks, in connection with the development of heat in the reaction chamber.

The heat flow gives rise to a temperature gradient across the Peltier elements. By operating the Peltier elements in reverse mode the flow of heat will generate a current from the Peltier elements which is proportional to the heat development in the reaction chamber.

Since the flow of heat from a body is proportional to its area it is advantageous to design the reaction chamber and the Peltier elements in such a way that a maximum contact area is created between them. In the first embodiment conventional (flat) Peltier elements have been employed, but in principle any geometry could be used.

In use of the biosensor unit a sample flow is fed through it, and unavoidably some heat from the reaction will escape from the reaction chamber with the outflow. However, by the suggested flat design of the reaction chamber substantially all heat from the reaction will be absorbed by the Peltier elements, and thus only a minute portion will leak out. Thereby a very high efficiency is obtained.

The geometry of the biosensor unit with regard to the analyte should be optimized for specific situations. As indicated above the biosensor unit can be designed in many ways, but from a production point of view, a flat configuration is probably preferable.

By virtue of the thermal separation of the heat sinks from the thermostated environment, the influence of external disturbances will also be reduced. This together with the fact that Peltier elements have a very low impedance, enables a very good signal to noise (S/N) ratio to be achieved. In addition, Peltier element do not require an external power source for excitation, which is the case for e.g. electrochemical biosensors.

Prior art thermal biosensors have utilized thermistors or thermo-couples as the temperature sensitive elements (transducer). Both of these have the drawback of a high impedance, and therefore susceptible of picking up noise.

By employing the design principles disclosed above, it is possible to construct a biosensor unit based on thermal detection with simplified production and with increased sensitivity, thereby simplifying the production process.

As an example a sample volume of e.g. 1 µl glucose with the concentration of 2 mmol/l (a low value in this regard) will yield a S/N in one of the present biosensor units of approximately 25:1. The corresponding value for thermistor based biosensors is rarely better then 5:1.

The simplified manufacturing process and the improved sensitivity are the main advantages of the present invention.

It should be emphasized that obvious combinations of features of the embodiments described above are within the scope of the invention. The scope of the invention is defined by the appended claims supported by the description and the annexed drawings.

The invention claimed is:

1. A biosensor system comprising:
    a pair of essentially flat heat sinks (9,10), arranged with their surfaces facing each other;
    a pair of Peltier elements (11) thermally attached to said heat sinks (9,10), one element (11) on each heat sink (9,10), on said facing surfaces; and
    a thermostated compartment (3,4,5),
    the heat sinks (9, 10) being suspended inside said compartment (3,4,5) by heat insulating members (8*a*,8*b*;160) connected to a respective block (3,4;80,100) such that heat exchange between the heat sink and the thermostated compartment (3,4,5) is kept minimal, wherein there is a gap between the Peltier elements (11) in which gap an insertable, generally flat biosensor unit (12) is positioned and fits snugly, said biosensor unit (12) comprising a reaction chamber in which a reaction is to be run, the heat of reaction of which can be measured by said Peltier elements, wherein the biosensor unit comprises thin foils (20;340) defining opposite walls of said reaction chamber (14;300) defined by the biosensor unit (12;260), a thickness of the reaction chamber being small in relation to dimensions of walls defined by the foils, the thickness being in an interval of 0.3-0.5 mm, and wherein the Peltier elements (11;200) are arranged so as to be in a heat conducting contact with said thin foils when the biosensor unit (12; 260) is in an operative position between the Peltier elements (11;200), and the heat conducting contact area between Peltier elements (11;200) and the foils (20;340) corresponds to the total reaction chamber wall area defined by said foils (20; 340), wherein a heat capacity of the heat sinks is selected such that a thermal impact from a heat flow in the heat sinks creates a thermal disturbance of an order of <1-100 ppm.

2. The biosensor system according to claim 1, wherein at least one of the Peltier elements (11;200) is movable to and from the other Peltier element (11;200) in order to facilitate insertion of the biosensor unit (12;260) between the Peltier elements (11;20).

3. The biosensor system according to claim 2, wherein the compartment (3,4,5) comprises a plurality of metal blocks (3,4,5;60,80,100), at least one of which acts as a thermostat element for the purpose of providing a generally constant air temperature around the heat sinks (9,10;140) and the Peltier elements (11;200) during operation of the biosensor system.

4. The biosensor system according to claim 1, wherein the compartment (3,4,5) comprises a plurality of metal blocks (3,4,5;60,80,100), at least one of which acts as a thermostat element for the purpose of providing a generally constant air temperature around the heat sinks (9,10;140) and the Peltier elements (11;200) during operation of the biosensor system.

5. The biosensor system according to claim 1, wherein one of the heat sinks (9) is moveable in relation to the block (3) connected thereto along the insulating member (8b) on which it is suspended.

6. The biosensor system according to claim 5, wherein the biosensor system further comprises a force element (18) exerting a force on the moveable heat sink (9) towards the other heat sink (10) for the purpose of pressing an inserted biosensor unit (12) against the other heat sink (10) and Peltier element (11).

7. The biosensor system according to claim 6, wherein the insulating members (8a,8b) comprise holding pins made of a material presenting a low heat conductivity.

8. The biosensor system according to claim 1, wherein the compartment (3,4,5) is defined by two opposing blocks (3,4) and a cylinder (5) located between said opposing blocks (3,4), each heat sink (9,10) being suspended on a respective one of the opposing blocks (3,4).

9. The biosensor system according to claim 8, wherein the insulating members (8a,8b) comprise holding pins made of a material presenting a low heat conductivity.

10. The biosensor system according to claim 1, wherein the biosensor system further comprises members (19,21) for snap fitting the biosensor unit (12) in its operative position.

11. The biosensor system according to claim 1, wherein the biosensor system further comprises suspension yokes (160) on said heat sinks (140), and journaling shafts (180) on which said yokes (160) rest to provide a pivot point for said heat sinks (140), whereby it is possible to widen the gap between the heat sinks (140) at one end, thereby facilitating insertion of a biosensor unit (12) between them.

12. The biosensor system according to claim 1, wherein each heat sink is a circular plate formed from a material having a large heat capacity.

13. The biosensor system according to claim 12, wherein the material is aluminum.

14. The biosensor system according to claim 1, wherein the heat sinks thermally float by provision of an air gap between the heat sinks, where thermally float means that heat exchange between each heat sink and the thermostated compartment is kept minimal.

15. The biosensor system according to claim 1, wherein the heat sinks are thermally insulated from their immediate environment so as to provide uniform heat flow from the reaction chamber to the heat sinks.

16. A biosensor system comprising:

a pair of essentially flat heat sinks (9,10), arranged with their surfaces facing each other, each heat sink being a circular plate formed from a material having a large heat capacity;

a pair of Peltier elements (11) thermally attached to said heat sinks (9,10), one element (11) on each heat sink (9,10), on said facing surfaces, each heat sink/Peltier forming a unit; and a thermostated compartment (3,4,5), the heat sinks (9,10) being suspended inside said compartment (3,4,5) by heat insulating members (8a,8b;160) connected to a respective block (3,4;80,100) so as to form an air gap between the heat sinks (9,10), whereby the heat sinks (9, 10) thermally float such that heat exchange between the heat sink and the thermostated compartment (3,4,5) is kept minimal, wherein there is a gap between the Peltier elements (11) in which gap an insertable, generally flat biosensor unit (12) is positioned and fits snugly, said biosensor unit (12) comprising a reaction chamber in which a reaction is to be run, the heat of reaction of which can be measured by said Peltier elements, wherein the biosensor unit comprises thin foils (20;340) defining opposite walls of said reaction chamber (14;300) defined by the biosensor unit (12;260), a thickness of the reaction chamber being small in relation to dimensions of walls defined by the foils, the thickness being in an interval of 0.3-0.5 mm, and wherein the Peltier elements (11;200) are arranged so as to be in a heat conducting contact with said thin foils when the biosensor unit (12; 260) is in an operative position between the Peltier elements (11;200), the heat conducting contact area between Peltier elements (11;200) and the foils (20;340) corresponds to the total reaction chamber wall area defined by said foils (20; 340), and the heat sinks are thermally insulated from their immediate environment so as to provide uniform heat flow from the reaction chamber (14;300) to the heat sinks, wherein a heat capacity of the heat sinks is selected such that a thermal impact from a heat flow in the heat sinks creates a thermal disturbance of an order of <1-100 ppm.

\* \* \* \* \*